(12) United States Patent
Bombin

(10) Patent No.: US 9,707,062 B2
(45) Date of Patent: Jul. 18, 2017

(54) CANNULAE FOR EVACUATING SALIVA AND/OR BLOOD FLOW

(71) Applicant: Medicotechnicare SA, Versoix (CH)

(72) Inventor: Jean Aymeric Bombin, Geneva (CH)

(73) Assignee: MEDICOTECHNICARE SA, Versoix (CH)

( * ) Notice: Subject to any disclaimer, the term of this patent is extended or adjusted under 35 U.S.C. 154(b) by 199 days.

(21) Appl. No.: 14/469,991

(22) Filed: Aug. 27, 2014

(65) Prior Publication Data
US 2015/0064646 A1    Mar. 5, 2015

(30) Foreign Application Priority Data
Aug. 28, 2013  (FR) ...................................... 13 01996

(51) Int. Cl.
*A61C 17/06* (2006.01)
*A61C 17/00* (2006.01)
*A61C 3/10* (2006.01)

(52) U.S. Cl.
CPC ............ *A61C 17/043* (2013.01); *A61C 17/00* (2013.01); *A61C 3/10* (2013.01)

(58) Field of Classification Search
CPC ...... A61C 17/04; A61C 17/043; A61C 17/046
See application file for complete search history.

(56) References Cited

U.S. PATENT DOCUMENTS

| 2,844,873 | A | * | 7/1958 | Bober | A61C 17/043 433/136 |
| 5,071,347 | A | * | 12/1991 | McGuire | A61C 19/001 433/91 |
| 6,736,640 | B1 | * | 5/2004 | Ellenbecker | A61C 17/043 433/138 |
| 2013/0095450 | A1 | * | 4/2013 | Ames | A61C 17/043 433/93 |

FOREIGN PATENT DOCUMENTS

FR    2 952 525 A1    5/2011
FR    2952525    *    5/2011

OTHER PUBLICATIONS

French Search Report and Written Opinion for FR Application No. 1301996; dated May 5, 2014.

* cited by examiner

*Primary Examiner* — George Evanisko
(74) *Attorney, Agent, or Firm* — Ulmer & Berne, LLP

(57) ABSTRACT

A cannula for evacuating irrigation fluid, saliva and/or blood for use in the dental field is formed of three interconnected tubular conduits and includes two hollow tube members one of which includes a first aperture formed on a buttressed plate parallel to the first tubular member, a second aperture being located on an upper part of the distal portion of the second tubular member allowing simplified placement and removal by engaging forceps in the apertures and use of the cannula with a first branch of the cannula inserted between the teeth and the tongue of a patient and the second branch of the cannula inserted between the teeth and the cheek of the patient.

20 Claims, 3 Drawing Sheets

CANNULAE FOR EVACUATING SALIVA AND/OR BLOOD FLOW

FIELD OF THE INVENTION

This application is based upon French Patent Application No. 13 01 996, filed August 28, 2013, the entire contents of which are herein incorporated by reference.

BACKGROUND OF THE INVENTION

Bucco-dental care or interventions are procedures performed in the oral cavity of a patient by a medical practitioner. The term "practitioner", means a dental surgeon, a dentist, and more generally any person called upon to perform a procedure in the bucco-dental sphere. The practitioner performs his or her intervention by introducing different types of instruments or utensils into the oral cavity. Bucco-dental interventions can involve operations aimed at maintaining healthy teeth or interventions involving dental surgery.

Now, as the mouth is used for respiration, for eating and for phonation it is a part of the human body which is fragile and hypersensitive. Thus, the internal tissue of the mouth concentrates in particular blood vessels and salivary glands which ensure lubrication of the oral cavity. Under such conditions, the practitioner works in an environment where saliva and blood can interfere with the work he is performing. This is especially true as the introduction of instruments into the oral cavity of the patient stimulates the defense mechanisms of the mouth, causing in particular overactity of the salivary glands. The removal of salivary flow and/or blood along with irrigation fluid or fluid for cooling dental instruments remains a problem that is constantly encountered during bucco-dental care.

Suction cannulae placed in the mouth of a patient undergoing a dental procedure are known, wherein such procedure involves the use of liquids, such as a medical fluid or water for irrigation. These liquids must be drawn off throughout the procedure. For this purpose, a suction cannula is positioned in the patient's mouth. This cannula consists of a hook-shaped tube connected to a suction source operating at low pressure. The tube is formed of two different plastic materials; the first material is flexible and the second, to allow shaping of the tube, has a greater hardness than the first. These cannulae however require the use of a "third hand" to hold the cannula. This "third hand" may be that of the practitioner's assistant or the patient. This makes practicing the operation more difficult, even dangerous in some cases, especially if the cannula is released during surgery.

French Patent Application FR-A-2560038 discloses a device for practicing odontostomatology affording protection to the tongue and cheek, as well as drawing off of saliva and coolants. The device includes a handle portion for holding the instrument. The practitioner must consequently hold the device with one hand. This may be a hindrance to the practitioner while performing various gestures during surgery on the patient.

There is therefore a need for an evacuation cannula for evacuating saliva and/or blood flow which is easier to use, notably a cannula which does not need to be held once placed in the patient's mouth.

SUMMARY OF THE INVENTION

These problems were solved by the cannula for saliva and/or blood flow evacuation subject of EP 09750155 filed May 14, 2009. The cannula disclosed and illustrated in that patent application solves virtually all the difficulties that arise in the cannulae considered above. Nevertheless, the present invention further improves the cannula as disclosed insofar as, firstly, it totally avoids any introduction of the hand into the mouth and, secondly, makes it possible to operate on small mouths or where opening of the mouth is limited or in the presence of the gag reflex, with the result that the practitioner no longer needs to introduce his fingers to the back of the mouth in order to place and remove the cannula, which is necessary in the case of the cannula according to EP 09750155.

Additionally, the cannula according to the present invention adapts itself better to the shape of the mouth and has the enormous advantage of being perfectly held in place and at the same time with enhanced stability. This has the effect of preventing movement of the cannula during surgery, which is a result not obtained in cannulae according to the prior art cited above.

The invention provides more particularly a cannula for removing irrigation fluid, saliva and/or blood flow for use in the dental field, formed of three tubular conduits connected together, consisting of:
  a first hollow tubular branch,
  a second hollow tubular branch,
  a hollow tubular arcuate portion, connecting these two branches, said cannula comprising:
    a first hollow tubular member having an axis substantially perpendicular to an axis of the first branch and into which a free end of the first branch opens,
    a second hollow tubular member forming an elbowed portion relative to the second branch, the axis of which is substantially perpendicular to an axis of said second branch, and into which a free end of the second branch opens and which is intended to be connected to suction means,
    at least one first aperture formed on a relief feature of the first tubular branch, and
    at least one second aperture formed on the second tubular member.

This cannula provides a dry surgical field, which is not invaded by irrigation fluids or saliva or blood. The cannula retains its position without the need to be maintained in place by hand whether this be by the practitioner, the practitioner's assistant or the patient. The practitioner can therefore perform the procedure with greater ease. Furthermore, the risk of the cannula falling during surgery is eliminated. The cannula is therefore safer to use. In addition, this cannula is quick and easy to install. The cannula is consequently easier to use for the practitioner while being reliable. It is also fully compatible with the presence of a dental dam.

According to an embodiment of the cannula according to the invention, the first aperture is located closer to the top of the hollow tubular arcuate portion than the second aperture.

In one embodiment of the cannula, the lengths of the first tubular branch and the second tubular branch are substantially equal.

In another embodiment of the cannula, the first hollow tubular branch is longer than the second hollow tubular branch. It is thus possible, when the cannula is positioned, for the first tubular member to rest on the floor of the mouth and the second tubular member to rest in the jugal trough.

According to yet another embodiment of the cannula according to the invention, a steel wire is embedded over the whole length of the three tubular branches.

Preferably, the cannula according to the invention is formed of a plastic material.

The present invention also provides a method for fitting a cannula of the aforementioned type according to the present invention, on the dental arch using clamp forceps.

More particularly, according to the present invention, this method for placing a cannula comprises providing a pair of clamp forceps; inserting each one of the active ends of the clamp forceps into a respective aperture of the cannula; introduce the cannula onto the dental arch using the clamp forceps; releasing the active ends of the clamp forceps from the apertures of the cannula so as to cause clamping of the cannula on the dental arch, and the first and second tubular members to come to bear respectively on the floor of the mouth and in the jugal trough of the patient. By the term active ends of the clamp forceps we mean those ends which are at the opposing end to the means by which the clamp forceps are grasped.

The clamp forceps can obviously be used to remove the cannula when the treatment session is completed.

The present invention also relates to the use of a cannula of the aforementioned type according to the present invention for the evacuation of irrigation fluid and saliva and/or blood flow during bucco-dental care or interventions, in which a first branch of the cannula is inserted between the teeth and the tongue of a patient and the second branch of the cannula is inserted between the teeth and the cheek of the patient, one of the hollow tubular members resting on the floor of the mouth and the other in the jugal trough of the patient.

The invention also provides apparatus for evacuating saliva and/or blood flow comprising:
  a cannula according to the invention,
  a suction source, and
  a suction pipe connecting the second tubular branch of the cannula to the suction source.

The invention further provides a method for the evacuation of irrigation fluid and saliva and/or blood flow during bucca-dental care or interventions using the cannula according to the invention in which a first branch of the cannula is inserted between the teeth and the tongue of a patient and the second branch of the cannula is inserted between the teeth and the cheek of the patient, one of the hollow tubular members resting on the floor of the mouth and the other in the jugal trough of the patient.

Other features and advantages of the invention will appear on reading the following detailed description of an embodiment of the invention, given by way of example only and with reference to the drawings.

DETAILED DESCRIPTION OF A PREFERRED EMBODIMENT

Figure 1:
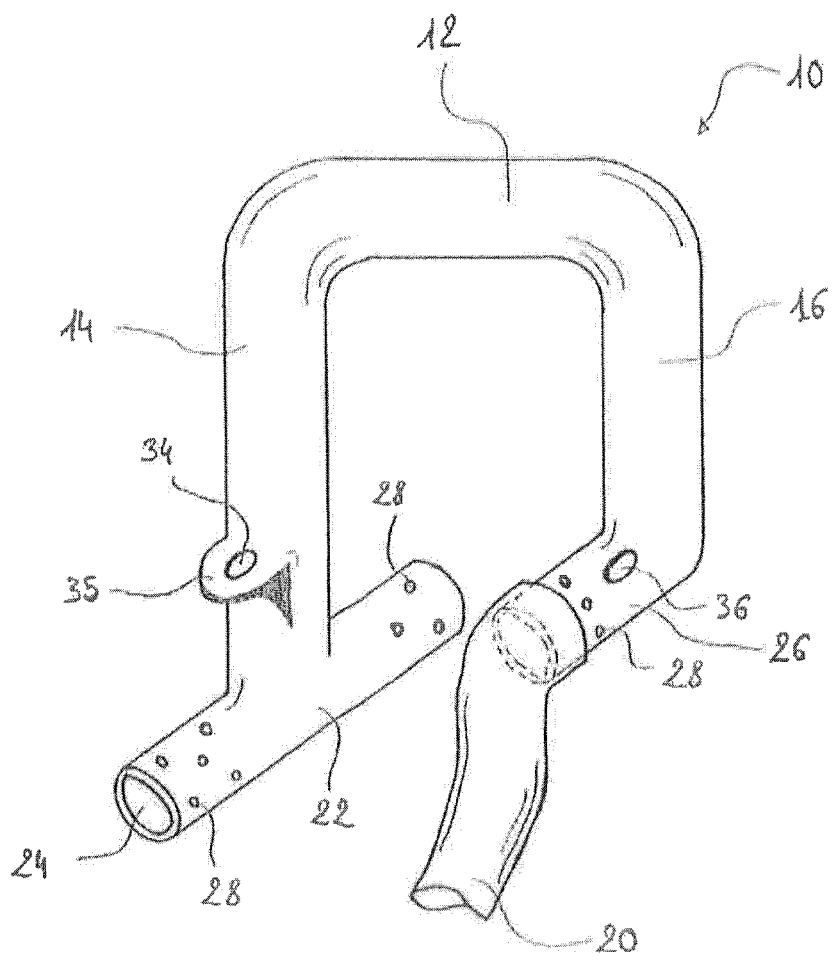
FIG. 1 is a diagrammatic view of an example of a cannula according to the invention.

The cannula 10 illustrated in FIG. 1 is a cannula or tube for evacuating saliva and/or blood flow and is intended to be used on a patient undergoing dental treatment.

The cannula 10 is formed of three tubular conduits, namely a first hollow tubular branch 14, a second hollow tubular branch 16 and a hollow arcuate tubular part 12 connecting the two branches. These three conduits form the cannula 10 having the general shape of a yoke or an inverted "U". The cross-section of the cannula 10 may be circular or oval and have a diameter of about 3 mm to 6 mm.

The arcuate shape of the cannula 10 as well as the presence of the first branch 14 enable the cannula 10 to be placed directly on the dental arch and to be maintained in position without it being held.

The first branch 14 of the cannula 10 terminates in a tubular member 22 formed of two portions situated on either side of the end of the first branch.

The tubular member 22 includes one or more suction holes 28 arranged on the upper surface of the tubular member 22, for example in staggered rows, to increase the efficiency of flow evacuation. For example, the suction holes 28 with a diameter of 1 mm may be staggered every 5 mm. Such a value is also a good compromise between ensuring the strength of the cannula 10 and efficiency of flow evacuation.

The second branch 16 of the cannula 10 has an end for connection to suction means. Such suction means may consist of a suction pipe 20. Suction pipe 20 is in general a transparent pipe. The pipe 20 is used to transmit a suction force used to suck saliva and/or blood flow and treatment fluids used during the dental procedure.

The cannula includes two apertures 34 and 36. The first of these apertures is a through hole 34 formed on a plate or stud 35 supported on the first branch 14 by buttressing means.

At least one second aperture 36 is formed on the upper face of the second hollow tubular member 26 which forms an elbow with the second branch 16, the distal end of the second hollow tubular member opening into the suction means 20. This second aperture 36 is located at a lower level than the level of the first aperture provided in the first branch 14. In other words, the first aperture can be located at a level closer to the top of the arched tubular portion 12 than the second aperture. The first branch 14 is, in the case shown, longer than the second branch 16.

The tubular member 26 includes one or more suction holes 28 arranged on its upper surface, for example in staggered rows, to increase the efficiency of flow evacuation. For example, the suction holes 28 with a diameter of 1 mm may be staggered every 5 mm. Such a value is also a good compromise between ensuring the strength of the cannula 10 and evacuation efficiency of the flow.

The second aperture 36 is in itself a suction orifice, and it is possible for two or more orifices similar to aperture 36 to be formed on the upper face of the second tubular member 26 forming an elbow with the second branch 16. Preferably, however, a single aperture 36 is disposed on the upper portion of the second tubular member 26 and suction holes 28 (not shown) are also provided there.

The cannula 10 may be made of any material that is sufficiently rigid and non-toxic to the soft tissue of the patient's mouth. Materials such as a metal (stainless steel, chrome plated brass) or a plastics or synthetic material (polyethylene, polyester, and polypropylene) can be used. The cannula 10 may in particular be made of plastics material. This will impart sufficient elasticity to the cannula 10 so that cannula 10 can be adapted to the patient's morphology. The cannula 10 can adapt to all possible anatomical cases. Furthermore, the plastics material allows manufacture by injection molding of cannulae for a moderate manufacturing cost. It then becomes possible to employ single-use cannulae 10 that are disposable. Discarding cannulae 10 after use avoids the sterilization step of cannula 10. In the case of a disposable cannula 10, it is even more advantageous for environmental purposes to employ recyclable plastics materials such as polyethylene or a cannula of biodegradable materials.

The cannula 10 can further comprise a steel wire embedded over the entire length of the tubular conduit forming the cannula. The steel wire is flexible thereby conferring the best possible matching of cannula 10 to the patient's anatomy.

Figure 2:
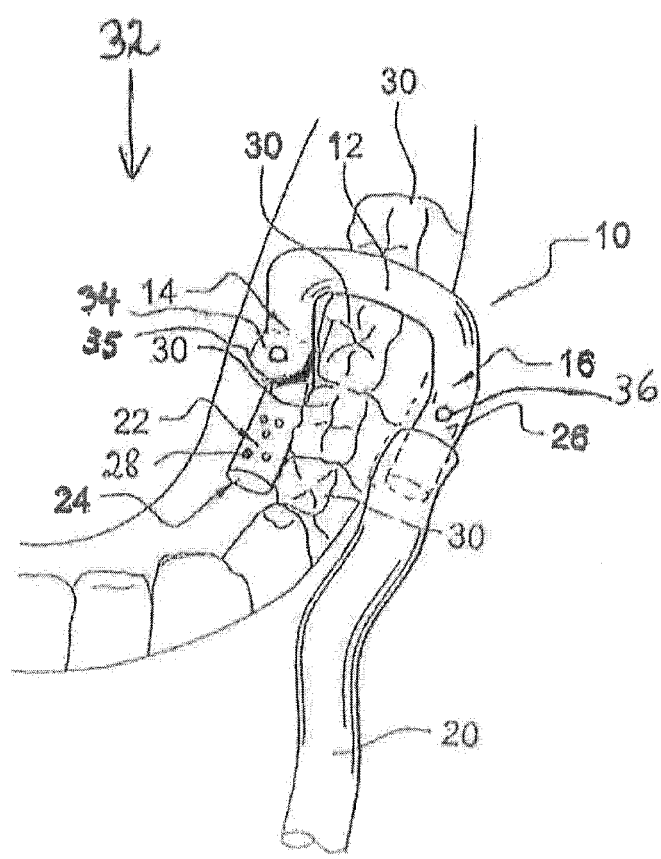
FIG. 2 is a diagrammatic view of the cannula of FIG. 1 positioned in the mouth of a patient.

As shown in FIG. 2 which illustrates the positioning of the cannula of FIG. 1 in the mouth of a patient, the first branch 14 of the cannula 10 is inserted between the patient's teeth 30 and tongue 32. The second branch 16 is inserted between the patient's teeth 30 and cheek (not shown in FIG. 2). The cannula is consequently well positioned on the dental arch in a straddling or spanning position. FIG. 2 shows the cannula positioned at the lower left side of the jaw, but of course a cannula exhibiting mirror-image symmetry can be positioned on the right side.

The end of the first branch 14 of the cannula 10 terminates in a tubular member 22 formed of two parts. This tubular member 22 is intended to rest on the floor of the mouth of the patient. As can be seen in FIG. 2, the lower surface of the tubular member 22 which rests on the floor of the mouth has no suction orifices. The surface where cannula 10 rests is treated to avoid any risk of injury ("piezo-trauma") and increase patient comfort. According to the example of FIG. 1, the axis of the tubular member 22 is orthogonal to the axis of the first branch 14 of cannula 10. This further improves retention of the cannula 10 in the patient's oral cavity. The tubular member 22 may however have a slight inclination with respect to a position perpendicular to the first branch 14 without this falling outside the ambit of the present invention. The tubular member 22 comprises, at least at one of its ends, preferably only at one of its ends, a suction orifice 24 for drawing off irrigation fluids and the patient's blood and/or salivary flow. Such a position avoids suction phenomenon which can cause discomfort, pain and/or create irritation or injury or damage to the floor of the mouth by simple piezo-trauma. In addition, leaving orifice 24 well clear avoids reducing the suction effect.

The orifice or orifices 24 may have a diameter of between 1 mm and 3 mm. Such values are a good compromise for a cannula 10 which is sufficiently strong and evacuates salivary flow and/or blood efficiently. When orifice 24 is too small, evacuation flow is inefficient; but, if the orifice 24 is too large, the strength and retention of cannula 10 are no longer guaranteed.

In the case of FIG. 1, the cannula 10 has two orifices 24, one at each end of the tubular member 22. Orifices 24 have a diameter of 1.5 mm. The advantage of this configuration is that the suction may be done in two opposite directions, which increases the efficiency of flow evacuation in the oral cavity.

Regarding the cannula shown in FIG. 1, the second branch 16 of the cannula 10 opens into the tubular member 26, which forms an elbow with the second branch 16 and the distal end of which is used to connect the cannula 10 to the suction means, which in the case shown are a suction pipe 20. The shape of the tubular member 26 and in particular its diameter are selected in accordance with the diameter of the suction pipe 20 to which the cannula 10 is connected.

The axis of tubular member 26 may extend in a direction substantially parallel to the axis of the tubular member 22 of the first branch. The suction pipe 20 connected to the tubular member 26 may then run parallel to the vestibule of the mouth up to the labial commissure to run outside the oral cavity. Such a configuration is consequently more ergonomic. Furthermore, support for cannula 10 is further improved. Suction pipe 20 can then descend towards the lateral face of the neck of the patient to the submandibular region. Suction pipe 20 can then be connected to a suction source allowing the flow to be drawn off through the orifice or orifices 24 of the cannula 10.

Figure 3:
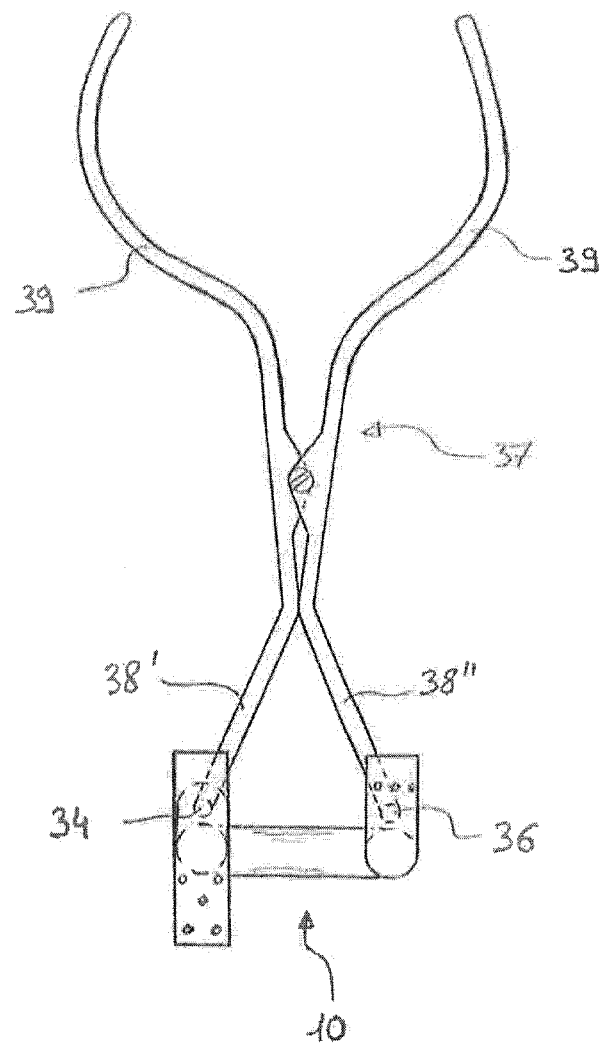
FIG. 3 shows the arrangement of the clamp forceps the active ends of which are inserted into first and second apertures to allow the dentist to place the cannula on the dental arch (or withdraw it).

FIG. 3 shows clamp forceps 37 in a position for cannula placement on the dental arch. The active ends 38' and 38" of the clamp forceps are introduced into the special apertures 36 and 34. The practitioner then introduces the cannula into the patient's mouth and places it on the dental arch so that the branches 14 and 16 (FIG. 2) are at either side of the arch, the cannula being astride the arch between the teeth and the cheek of the patient, one of the hollow tubular members resting on the floor of the mouth and the other in the jugal trough of the patient. Upon removing the active ends from the apertures 36 and 34, clamping of the cannula on the dental arch occurs. The cannula is thus held securely in place with greater stability thereby preventing movement of the cannula during the dental procedure. By the term active ends of the clamp forceps we mean those ends which are at the opposing end to the means 39 by which the clamp forceps are grasped.

The embodiments described above and the drawings should be considered as illustrative and not limiting, and the invention is not intended to be limited to the details given herein but may be modified within the scope of the appended claims.

What is claimed is:

1. An apparatus for use in the dental field comprising:
a cannula, the cannula including;
  a) a first hollow tubular branch,
  b) a second hollow tubular branch,
  c) a hollow tubular arcuate portion connecting the first hollow tubular branch and the second hollow tubular branch,
  d) a first hollow tubular member having an axis substantially perpendicular to an axis of the first hollow tubular branch and into which a free end of the first hollow tubular branch opens,
  e) a second hollow tubular member forming an elbowed portion relative to the second hollow tubular branch, the axis of the second hollow tubular member being substantially perpendicular to an axis of the second hollow tubular branch, and into which a free end of the second hollow tubular branch opens and which is configured to be connected to suction,
  f) a relief feature on the first hollow tubular branch, the relief feature being a stud projecting laterally from the first hollow tubular branch, wherein at least one first aperture is formed in t he stud, and
  g) at least one second aperture formed on the second hollow tubular member, the at least one first aperture being positioned on the stud above and offset from the at least one second aperture, wherein the at least one first aperture and the at least one second aperture are configured to be engaged by each one of the active ends of a clamping forceps for positioning of the cannula, wherein the at least one second aperture is fluidly connected with the second hollow tubular member such that the at least one second aperture is operatively configured for suction.

2. The apparatus of claim 1 wherein the first aperture is more proximate the hollow tubular arcuate portion than the second aperture.

3. The apparatus of claim 1, wherein the lengths of the first hollow tubular branch and the second hollow tubular branch are substantially equal.

4. The apparatus of claim 1, wherein the first hollow tubular branch is longer than the second hollow tubular branch.

5. The apparatus of claim 1, wherein the first tubular member comprises one or more suction holes arranged on the surface of the first tubular member.

6. The apparatus of claim 1, wherein the second tubular member comprises one or more suction holes arranged on the surface of the second tubular member.

7. The apparatus of claim 1, wherein a steel wire is embedded over substantially the whole length of the cannula.

8. The apparatus of claim 1, wherein the cannula is formed of a plastic material.

9. The apparatus of claim 1, wherein the cannula has a diameter of from about 3 mm to about 6 mm.

10. The apparatus of claim 1, wherein the hollow tubular arcuate portion has a substantially U-shaped configuration.

11. The apparatus of claim 1, wherein the first tubular member includes a plurality of suction holes in a staggered relationship.

12. The apparatus of claim 11, wherein each of the plurality of suction holes has a diameter of about 1 mm.

13. The apparatus of claim 1, wherein the second tubular member includes a plurality of suction holes in a staggered relationship.

14. The apparatus of claim 13, wherein each of the plurality of suction holes has a diameter of about 1 mm.

15. The apparatus of claim 1, further comprising a suction pipe selectively coupled with the second hollow tubular member.

16. The apparatus of claim 1, wherein the cannula is disposable.

17. The apparatus of claim 1, further comprising clamp forceps selectively coupled with the cannula.

18. The apparatus of claim 17, wherein the at least one first aperture and the at least one second aperture selectively engage the clamp forceps.

19. The apparatus of claim 1, wherein the first hollow tubular member defines a first orifice and a second orifice, wherein the first orifice is substantially coaxial with the second orifice.

20. The apparatus of claim 1, wherein the first hollow tubular member defines a first orifice and a second orifice, wherein the first orifice is offset from the second orifice.

* * * * *